United States Patent [19]

Thurmond et al.

[11] Patent Number: 5,259,836
[45] Date of Patent: Nov. 9, 1993

[54] HYSTEROGRAPHY DEVICE AND METHOD

[75] Inventors: Amy S. Thurmond; Josef Rösch, both of Portland; Barry T. Uchida, Lake Grove, all of Oreg.

[73] Assignee: Cook Group, Incorporated, Bloomington, Ind.

[21] Appl. No.: 635,354

[22] Filed: Dec. 21, 1990

Related U.S. Application Data

[63] Continuation of Ser. No. 467,940, Jan. 22, 1990, abandoned, which is a continuation of Ser. No. 271,933, Nov. 16, 1988, abandoned, which is a continuation-in-part of Ser. No. 226,059, Jul. 29, 1988, abandoned, which is a continuation-in-part of Ser. No. 126,778, Nov. 30, 1987, abandoned, said Ser. No. 271,933, is a continuation of Ser. No. 251,195, Sep. 29, 1988, abandoned.

[51] Int. Cl.$^5$ .................. A61M 31/00; A61M 25/00
[52] U.S. Cl. ...................................... 604/55; 604/176
[58] Field of Search ................... 604/54, 55, 93, 176; 606/193; 128/654, 653 R, 657, 658, 4, 6, 7, 778

[56] References Cited

U.S. PATENT DOCUMENTS

| | | |
|---|---|---|
| 3,048,175 | 8/1962 | Uddenberg . |
| 3,096,764 | 7/1963 | Uddenberg . |
| 3,685,509 | 8/1972 | Bentall ........................ 604/176 X |
| 3,721,229 | 3/1973 | Panzer . |
| 3,926,192 | 12/1975 | Van Maren . |
| 4,430,076 | 2/1984 | Harris ................................. 604/96 |
| 4,474,576 | 10/1984 | Gobby ............................... 604/176 |
| 4,606,336 | 8/1986 | Zeluff . |

FOREIGN PATENT DOCUMENTS

| | | |
|---|---|---|
| 2578427 | 3/1985 | France . |
| 0709077 | 1/1980 | U.S.S.R. .............................. 604/176 |

OTHER PUBLICATIONS

"Fallopian Tube Obstruction: Selective Salpingography and Recanalization", Radiology, vol. 163, May 1987, pp. 511-514.
"Selective Transcervical Fallopian Tube Catheterization: Technique Update", Radiology, vol. 168, No. 1, Jul. 1988, pp. 1-6.
"The VUC-Instrument Vacuum-Uterine-Cannula by Malmstrom-Thoren for Hysterosalpingography and Insufflation" sales brochure distributed by A. B. Vacuum Extractor, Inc., 4 Plympton Street, Woburn, Mass. 01801.
"Fluoroscopic Transcervical Fallopian Tube Catheterization for Diagnosis and Treatment of Female Infertility Caused by Tubal Obstruction", RadioGraphics, vol. 8, No. 4, Jul. 1988, pp. 621-640.
Rösch, J., A. S. Thurmond, B. T. Uchida, "Diagnosis and Treatment of Fallopian Tube Obstruction with Selective Salpingography and Catheter Recanalization", study from the Dept. of Diagnosis Radiology School of Medicine, Oregon Health Sciences Univeristy, May 1987.
"Techniques and Compilations of Hysterosalpingography", Chapter 2, Diagnostic Imaging of Infertility, pp. 2-26, 1987.
"Transcervical Balloon Tuboplasty", Fertility & Sterility, vol. 46, No. 5, Nov. 1986, pp. 963-966.
"Transvaginal Fluoroscopic Recanalization of a Proximally Occluded Oviduct", Fertility & Sterility, vol. 44, No. 5, Nov. 1985, pp. 704-706.

Primary Examiner—John D. Yasko
Assistant Examiner—Adam J. Cermak
Attorney, Agent, or Firm—Woodard, Emhardt, Naughton, Moriarty & McNett

[57] ABSTRACT

A hysterography device is provided which avoids the various disadvantages inherent in prior art devices, namely patient discomfort, incomplete seal-off of the cervical canal, complexity, and lack of provision for introduction of catheters or filberoptic devices into the uterine cavity through a sterile conduit. A handle having a conduit therein is provided for the introduction of catheters, coaxial catheter systems, fiberoptic devices, and contrast media. A cup at the distal end of the handle is vacuum or suction seated on the cervix of the patient to seal contrast media in the cervical canal. A movable cone may be provided for an enhanced seal. Preferably, the cup and the handle are soft and flexible plastic allowing for better seating on the cervix and better operator manipulation. A variety of cup shapes and sizes may be used. Vacuum suction in the cup may be provided by an independent flexible conduit. A method of use of such device is provided.

17 Claims, 8 Drawing Sheets

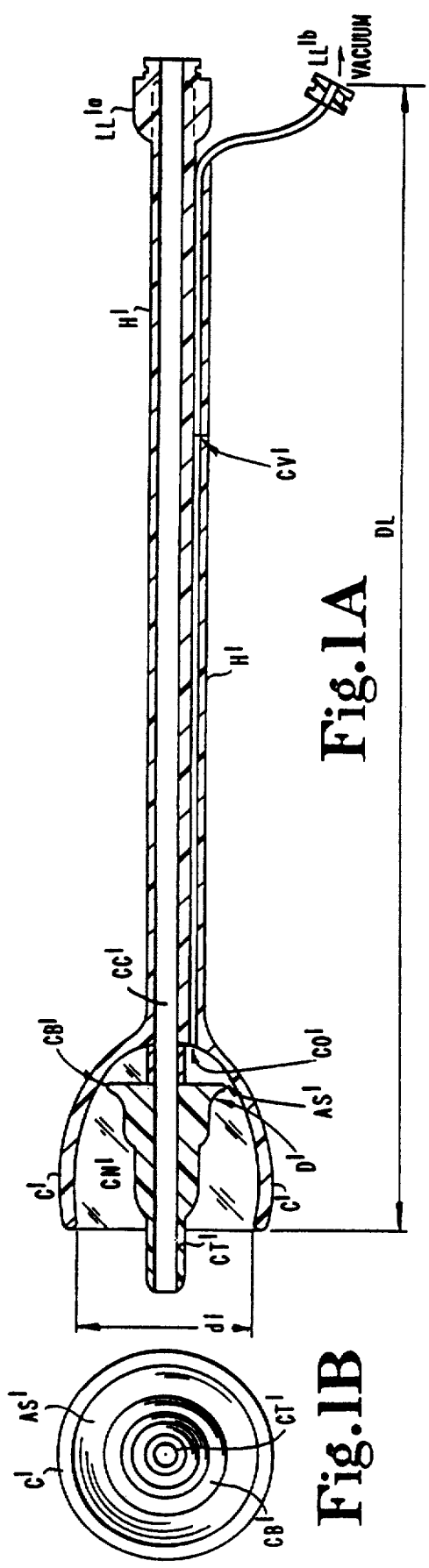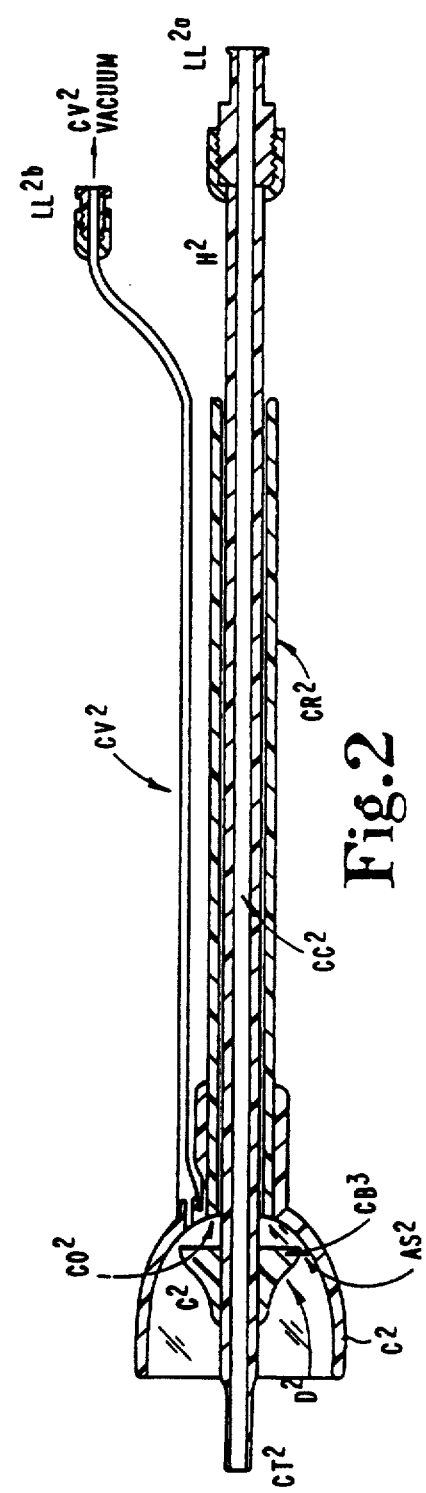

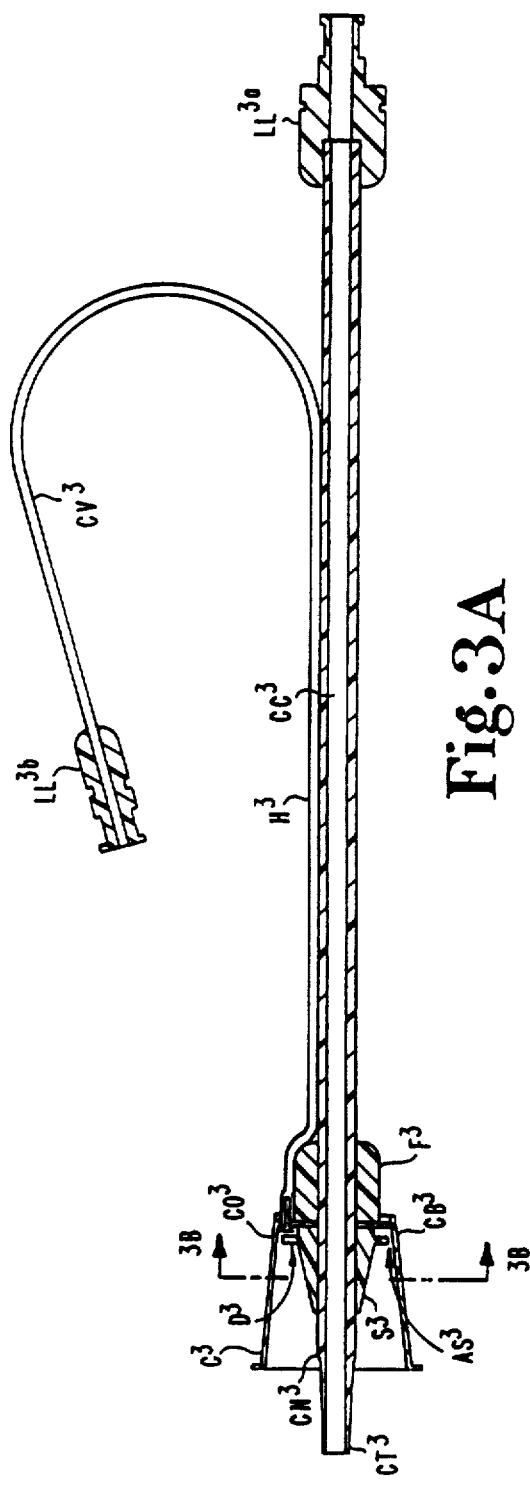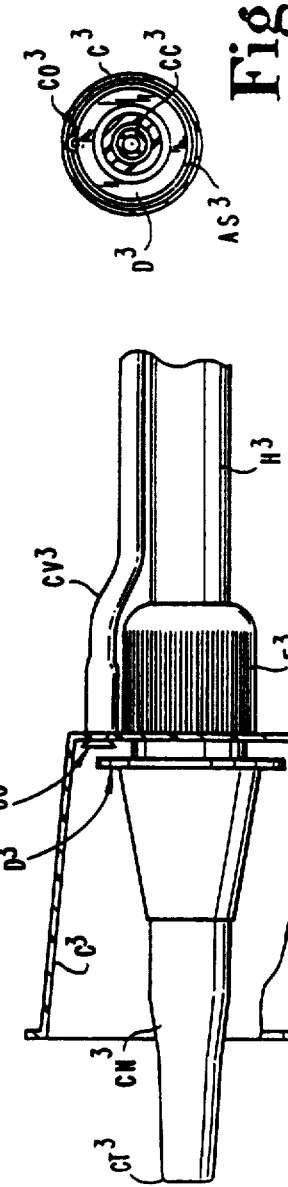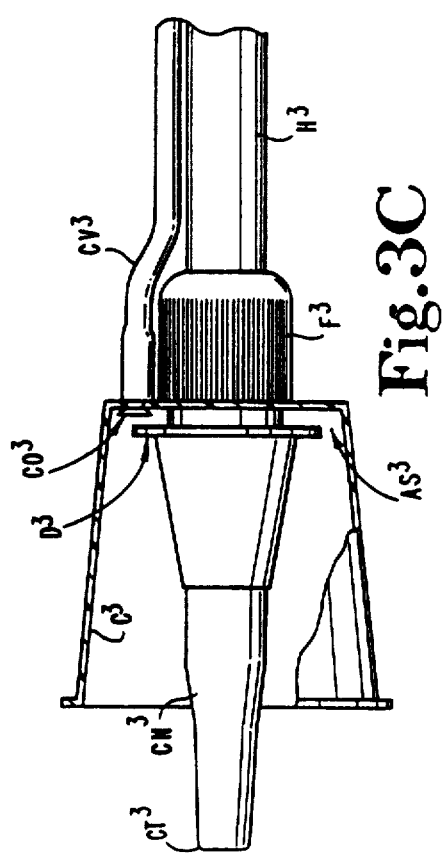

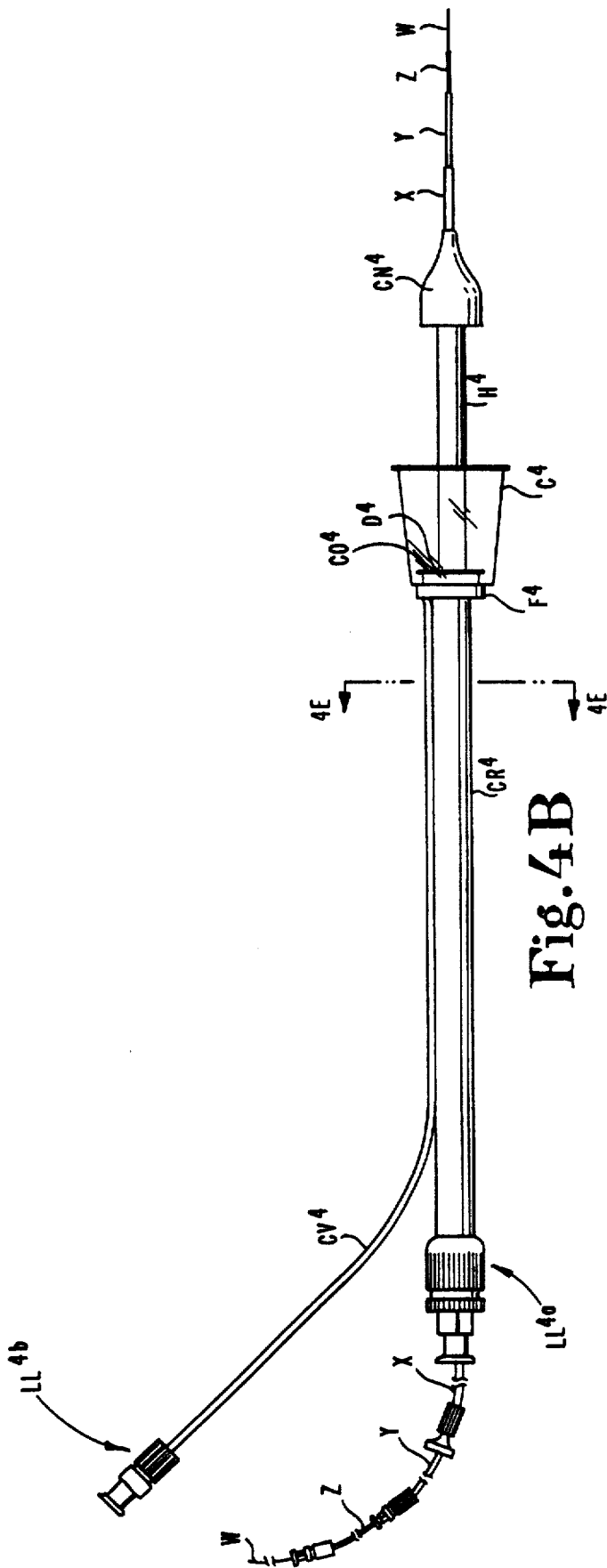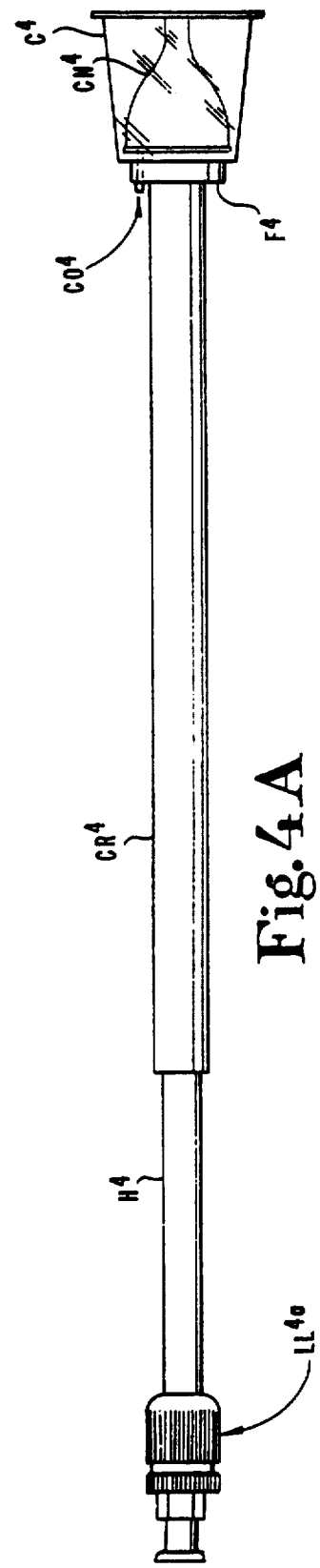
Fig.4B
Fig.4A

HYSTEROGRAPHY DEVICE AND METHOD

RELATED APPLICATIONS

This application is a continuation of pending U.S. patent application Ser. No. 467,940 filed Jan. 22, 1990 (now abandoned) which is a continuation of U.S. patent application Ser. No. 271,933 filed Nov. 16, 1988 (now abandoned) which is a continuation of U.S. patent application Ser. No. 251,195 filed Sep. 29, 1988 (now abandoned); 07/271,933 is a continuation-in-part of Ser. No. 07/226,059, filed Jul. 29, 1988 (now abandoned), which is a continuation-in-part of Ser. No. 07/126,778, filed Nov. 30, 1987 (now abandoned).

BACKGROUND OF THE INVENTION

This invention pertains to a device providing a sterile conduit for non-invasive entry into the uterine cavity.

A number of conditions require non-invasive entry into the uterine cavity, for both therapeutic and diagnostic purposes. Such access is provided through the canal of the uteral cervix, transvaginally. For diagnostic purposes, contrast media may be injected into the cervical canal and radiography carried out, both to establish the outline of the uterine cavity and/or patency of the Fallopian tubes. Alternatively, ultrasonography can be used following gas insufflation, or a fiberoptic device can be introduced into the uterine cavity for direct inspection. Yet another means of providing access is to introduce catheters into the cervical canal, and input contrast media into the uterine cavity directly.

Recently described in an article entitled "Fallopian Tubes Obstruction: Selective Salpingography and Recanalization," Radiology, May 1987, number 167, pp. 511-514, is the use of a coaxial catheter system with a wire guide for transvaginal recanalization of stenosed Fallopian tubes, also carried out through the cervical canal. This procedure usually is performed in conjunction with diagnostic radiography prior to and following recanalization. Inasmuch as the stenosis usually is a result of inflammatory changes and is one major cause of female infertility, and since surgical transabdominal recanalization of the Fallopian tubes has been shown to meet with only limited success, development of new instrumentation enabling use of non-invasive procedures, such as the radiological approach, is of major importance.

Non-invasive access to the Fallopian tubes is also utilized for the purpose of artificial insemination. Typically, this procedure, which has been shown to be at least twice as effective as in vitro fertilization, involves harvesting the egg and injecting a mixture of sperm and egg into the Fallopian tubes. While this procedure can be carried out under hysteroscopic, radiographic, or ultrasonographic control, the common denominator of all these procedures is access through the cervical canal and insertion of catheters into the tubes. Another possible use of selective tubal catheterization is to inject compositions for the purpose of reversible sterilization.

The internal genital organs must be protected from infectious agents normally or pathologically present in the vaginal environment. A reliably attachable conduit system for safe introduction and manipulation of catheters and other devices, and for the introduction of radiographic contrast media into the uterine cavity and the tubes for the purpose of radiography, does not yet exist. Devices for the introduction of radiographic contrast media for the purpose of uterine/tubal radiography have been described previously, but they have a number of drawbacks, and they do not allow introduction of catheters.

One prior art approach involves grasping the cervix with a tennacula and inserting a rubber cannula into the cervix under tension, with the distinct disadvantages of discomfort to the patient and bleeding from the cervix, as well as incomplete sealing of the cervical canal.

Another prior art device is a large diameter catheter ("Foley catheter") equipped with an occluding balloon into the cervical canal. While sealing with the balloon's inflation is adequate, the Foley catheter does not permit rectification of the uterus by traction, which is often necessary for radiodiagnostic presentation.

Another prior art device, "Malmstrom's cannula", employs a cup appositioned to the cervix and held in position by vacuum, forcing a conical rubber cannula into the canal. The seal is accomplished by pressure against the cervical mucosa, but this is not always successful, especially when the entrance to the cervix has been lacerated by previous births. Also, the device is complicated, consisting of a large number of parts and requiring considerable manipulation for each resterilization which can be carried out only after thorough dismantling and cleaning. The device does not allow insertion of a catheter.

Another prior art device is the Kidde cannula, devised to seal the canal's orifice with a rubber cone, and to enter the uterine canal with steel tubing. This poses a risk of injury to the uterine cavity, as described, for example, by Winfield, A. C. and Wenz, A. C., "Techniques and Complications of Hysterosalpingography," in Williams and Wilkins (eds.), Diagnostic Imaging of Infertility, 1987, pp. 9-26. This device does not permit introduction of a coaxial or single catheter for selective tubal catheterization or fiberscope introduction.

SUMMARY OF THE INVENTION

In accordance with the teachings of this invention, a hysterography device and method is provided which avoids the various disadvantages inherent in prior art devices, namely patient discomfort, incomplete seal-off of the cervical canal, complexity of the device, and lack of provision for introduction of catheters or fiberoptic devices.

The present invention also provides a hysterography device comprising: a handle containing one or two conduits; a cup located at a first end of the handle, the cup designed to fit the cervix of a patient; means for applying a vacuum within the cup, made from soft plastic material; a cone located within the cup having a nose designed to penetrate into the introitus of the cervical canal of the patient.

The present invention also provides a hysterography device comprising: a handle containing a first conduit; a cup located at a first end of the handle, the cup designed to fit the cervix of a patient, the cup being made of a soft plastic material; means for applying a vacuum within the cup; and a cone located within the cup having a nose designed to penetrate into the introitus of the cervical canal of the patient.

The present invention also provides a hysterography device comprising: a handle containing a first conduit, the handle being made of a plastic material and being flexible to allow operator manipulation thereof; a cup located at a first end of the handle, the cup designed to fit the cervix of a patient; means for applying a vacuum within the cup; and a cone located within the cup having a nose designed to penetrate into the introitus of the cervical canal of the patient.

The present invention also provides a hysterography device comprising: a handle containing a first conduit; a cup located at a first end of the handle, the cup designed to fit the cervix of a patient; means for applying a vacuum within the cup; a cone located within the cup having a nose designed to penetrate into the introitus of the cervical canal of the patient; and a catheter in the first conduit.

The present invention also provides a method of providing non-invasive entry into the uterine cavity of a patient, comprising the steps of suction sealing a cup of a hysterography device to the cervix of the patient, the hysterography device having a handle with a first conduit therein; introducing a catheter having a lumen through the first conduit and into the uterine cavity of the patient.

An object of the present invention is to provide an improved hysterography device and method.

Related objects are apparent from the following description.

BRIEF DESCRIPTION OF THE DRAWINGS

FIG. 1A is a cross-sectional view of a first embodiment of this invention;

FIG. 1B is an end view of the embodiment of FIG. 1A;

FIG. 2 is a cross-sectional view of a second embodiment of this invention;

FIG. 3A is a cross-sectional view of a third embodiment of this invention;

FIG. 3B is a cross-sectional view of the third embodiment of this invention taken from the perspective of line 3B—3B in FIG. 3A.

FIG. 3C is a detail, partially cutaway side view of the distal end of the third embodiment of this invention;

FIG. 4A is a side view of a fourth embodiment of this invention in a first mode;

FIG. 4B is a side cross-sectional view of the fourth embodiment of this invention in a second mode;

DETAILED DESCRIPTION

Figure 4D:
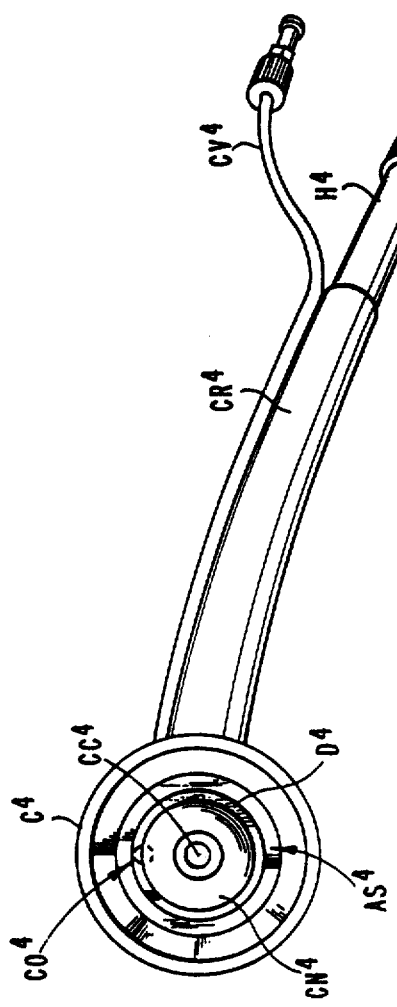
FIG. 4D is an end view of the fourth embodiment of this invention.
Figure 4E:
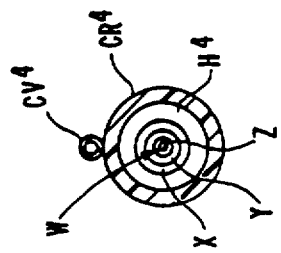
FIG. 4E is a cross-sectional view of the fourth embodiment of this invention taken from the perspective of line 4E—4E in FIG. 4B.
Figure 4C:
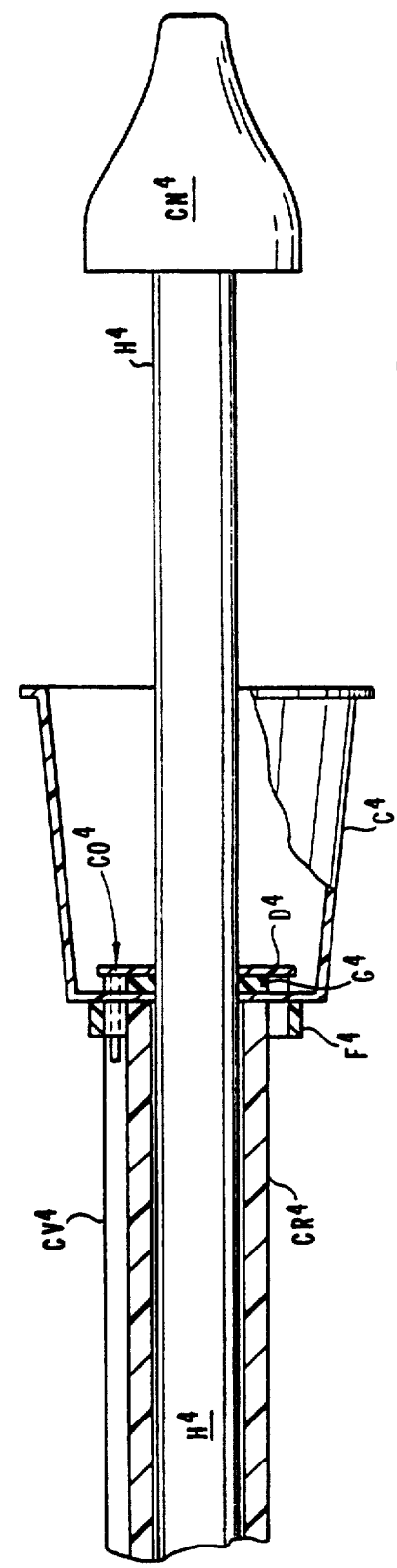
FIG. 4C is a detailed, partial outaway side view of the fourth embodiment of this invention.

This invention is unique in that a novel device operates in consonance with physiological factors that are dynamic rather than morphological. Thus, the circular musculature of the cervix can be stretched by pressure exerted on the walls of the cervical canal. Such "cervical dilation" is undesirable for a seal-off. The novel device utilizes a conduit of increasingly larger diameter which dilates the canal but minimally, while the canal's dilation is to an extent prevented, compressing the circumference of the cervix, which results from the vacuum by forcing the cervix into a conical cup.

In the drawing figures and specification, the reference characters used in the four embodiments are the same for similar elements, except for the use of the superscripts, 1, 2, 3, and 4 corresponding respectively to the first, second, third, and fourth embodiments. As shown in the Figures, a hysterography device constructed in accordance with the teachings of this invention includes, preferably, conduit CC which is formed along the longitudinal axis of the device, which serves as the aids, rigid or flexible leading handle H, at the top of which is cup C, designed to fit the cervix. Cup C is cylindrical in its distal portion but, over radius, becomes progressively more conical towards its base CB. The cup is made preferably from a pliable material, to allow its best adaptation to the cervix. Base CB is flat or recessed, and placed over the outlet CO (of conduit CV) through which vacuum generated by a negative pressure device is applied. This results in suction which forces the cervical mucosa against the edge of the cup, and or the cervix into the cup.

Concentrically and centrally placed into cup C along the axis provided by conduit CC is cone CN whose proximal, straight part is designed to penetrate into the introitus of the cervical canal. The diameter of the cone is then gradually or stepwise increased to provide the primary seal within the canal. As the inner cone CN is pressed into the cervical canal, its increasingly greater diameter produces the secondary seal-off. Thus, the more vacuum is applied, the more the peripheral mucosa is rolled against and pressed against the inner wall of cup C, thus providing the secondary seal. Finally, the perpendicular part D of the cone, while being forced against the frontal mucosa of the cervix, acts as a third sealing surface. The cone can be produced either as one piece, or constructed from several components, with the cup either affixed to the handle H (FIGS. 1A, 1B, 3A, and 3B) or to a collar $CR^2$, $CR^4$ surrounding the handle H (FIGS. 2, 4A, 4B, 4C, 4D, 4E and 4F).

While a version of the hysterograph with the cup affixed to handle H and thus providing a fixed longitudinal relation between the tip of the conduit and the cup is useful predominantly for diagnostic purposes, a version employing a movable cup is useful when an anatomical irregularity is encountered for interventional procedures, such as selective or sub-selective catheterization. Such procedures involve manipulations, often resulting in dilation of the cervical canal. When this happens, deeper penetration of the conduit CC into the canal is necessary to provide a seal-off, without which a post-procedural diagnostic radiography could not be carried out. This can be accomplished in a "movable cup" version of the with cone $CN^2$ and $CN^4$, shown in the second and fourth embodiments of this invention, by sliding the collar such as $CR^2$ or $CR^4$, and thus the affixed cup, away from the tip of conduit CC. In the fourth embodiment, cone $CN^4$ may by moved as much as 5.5 cm in a direction away from cup $C^4$. A seal between the collar CR and handle H is provided by a seal-fit of the diameters; to increase the seal, a silicone or other physiologically inert lubricant can be utilized. Conveniently, cups of several sizes can be interchangeable on the same instrument.

Central conduit CC is contained in the handle H and provides a passage through which a catheter, a coaxial catheter system, or fiberoptic device can be inserted, or through which contrast media can be injected. As set forth in the incorporated May 1987 Radiology article above, one specific selection for such coaxial catheter system may comprise a first, outer catheter X having a second catheter Y therein, and further having a third catheter Z inside the second catheter (See FIGS. 4B, 5A, 5B and 5C). A wire guide W, such as a Cope-type guide wire with a flexible tip, may be located inside the third catheter. Various catheters and guide wires may be used as set forth, for example a 5-F polyethylene Torcon catheter, a 3-F Teflon catheter and a Cope-type wire guide, 0.018 and 0.025 inches (0.046 and 0.064 cm) in diameter, offered by Cook Incorporated of Bloomington, Ind. Guide wires made of a mandrel of 0.035 inch (0.089 cm) LLT-type wire onto which an 8 cm long, 0.018 or 0.025 inch wire is soldered, also offered by Cook Incorporated may be used. The tip of such guide wire may be soft and flexible platinum or other suitable material. A set of suitable catheters and guide wires offered by Cook Incorporated of Bloomington, Ind. has been developed for this invention. The set includes: 1) for catheter X, a 9.0 French radiopaque Teflon catheter which is 31.5 cm long and has a Check-Flo valve; 2) for catheter Y, a 5.5 French radiopaque braided polyethylene torque control catheter which is 50 cm long with a 3 cm non-braided tip; 3) for catheter Z, a 3.0 French radiopaque Teflon catheter which is 65 cm long; and 4) for the guide wire W, both a Cope Mandrel Wire Guide having a 0.38 mm diameter and a 90 cm length and made of stainless steel with a platinum tip, and a Curved Safe-T-J wire guide with a 0.89 mm diameter and a 90 cm length with a 1.5 mm Safe-T-J tip and being made of stainless steel. The set also includes a Tuohy-Borst Adapter for the Hysterograph.

At the distal end of conduit CC, a standard Luer lock $LL^a$ is provided to afford attachment of standard syringes and/or catheter collars. The handle H is rigid or flexible and made from a plastic tube containing one or two lumina, one for CC and one for vacuum. Alternatively, the vacuum line can be an independent tube.

If desired, the device conveniently consists of one or several parts, and the cup can be manufactured from suitable see-through plastic materials to allow viewing of the insertion of the conus. The device can be machined and assembled from commercially available components, or molded and produced entirely or in part by standard plastic extrusion methods. Suitable plastic materials include polycarbonate, polyacrylic resins, clear polyethylene, polyvinyl chloride, carbon fiber, fiberglass, and other organic and inorganic polymeric or monomeric compositions.

The devices, intended to fit a wide range of cervical sizes, are easily manufactured and conveniently sterilized and packaged ready for one-time use or repeated use.

The devices can be constructed to have a range of dimensions, as follows:

| Dimension | Approximate Range of Values | Approximate Value in One Embodiment |
|---|---|---|
| Overall length of device (DL) | 220 to 300 mm | 240 mm or 260 mm |
| Outside diameter of cup C (do) | 25 to 40 mm | 33 mm |
| Inside diameter of cup C (di) | 21 to 36 mm | 25 mm or 30 mm |
| Length of cup C | 25 to 35 mm | 26 mm or 27 mm |
| Diameter of conduit | 2 to 5 mm | 2.6 mm (at the tip) |

| Dimension | Approximate Range of Values | Approximate Value in One Embodiment |
|---|---|---|
| Length of cone CN | 20 to 40 mm | 20 mm or 35 mm |
| Outside diameter of base CB of cone CN | 15 to 25 mm | 20 mm |
| Outside diameter of tip CT of cone CN | 3 to 6 mm | 4 mm |
| Outside diameter of handle H (may be oval) | 6 to 12 mm | 7 mm |
| Length of collar CR | 5 to 17 mm | 15 mm |
| Diameter of collar CR | to seal-fit the outer surface of handle H | |

Various structural differences between the various illustrated embodiments are shown. For example, the cups of the first and second embodiments, $C^1$ and $C^2$, have more curved or generally parabolic shape as compared to the cups with generally straight side walls of the third and fourth embodiments, $C^3$ and $C^4$. Accordingly, these cups, $C^3$ and $C^4$, have a generally straight profiled side wall defining a frustum of a cone. Furthermore, the shape and arrangement of the various perpendicular parts D varies between embodiments. For example, part $D^3$ is formed as part of an elongated conical saddle $S^3$ around nose $CN^3$. Part $D^4$ is affixed to cup $C^4$, independent of cone $CN^4$ and of handle $H^4$, so that upon movement of cup $C^4$ with respect to cone $CN^4$, part $D^4$ will remain a constant spacing with respect to cup $C^4$. Part $D^4$ and the base of the cup define an annular space $AS^4$ therebetween. This annular space is in front of the opening $CO^4$ and serves to more evenly distribute the suction action of the vacuum around the inner circumference of the cup $C^4$. Similar annular spaces, $AS^1$, $AS^2$, and $AS^3$, in the other embodiments perform similar functions. Also, note that in FIG. 4A, conduit $CV^4$ has been removed, showing the stainless steel cannula which partially defines opening $CO^4$.

FIG. 4D shows an end view of the invention with the flexible handle $H^4$ and the flexible collar $CR^4$ flexed somewhat about the longitudinal axis of the handle.

Figure 4F:
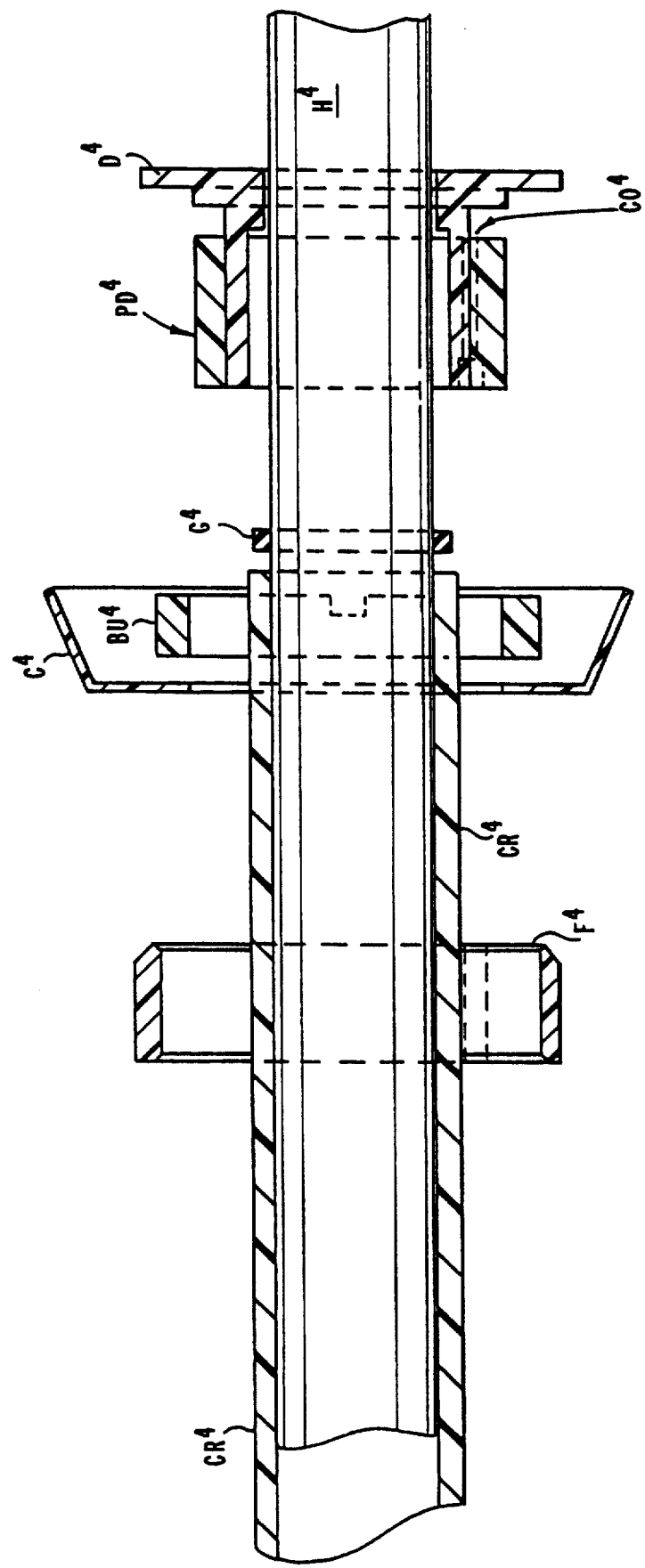
FIG. 4F is an exploded side cross-sectional detail of the fourth embodiment of this invention.

FIG. 4F shows an exploded detail view of one construction used to couple flexible, plastic collar $CR^4$ with cup $C^4$. Collar $CR^4$ is inserted through a hole cut in the base of cup $C^4$, with handle $H^4$ positioned therein. Ultrasonic welding is used to connect parts together. For example, in the fourth embodiment, fitting $F^4$, bushing $BU^4$, part $PD^4$ and part $D^4$ (see FIG. 4F) are ultrasonically welded together, helping to form the assembly connecting collar $CR^4$, cup $C^4$ and perpendicular part $D^4$ together. Gasket $G^4$ provides a fluid seal around handle $H^4$.

The various parts to be assembled together are preferably glued by suitable adhesives, such as Loctite 401, VC-1 or the like. For example, in the third embodiment, fitting $F^3$ and perpendicular part $D^3$ are glued to handle $H^3$ with such adhesives. Fluid tight seals around the cup may be provided by a sealant such as silicone GE RTV #118 or similar sealants. Also, it is preferable to remove, by cutting or abrasion, any sharp bead which may exist on the inside diameter of the cup, such as cup $C^3$, near the outer lip thereof to provide for a better seal with the patient's cervix.

Figure 5A:
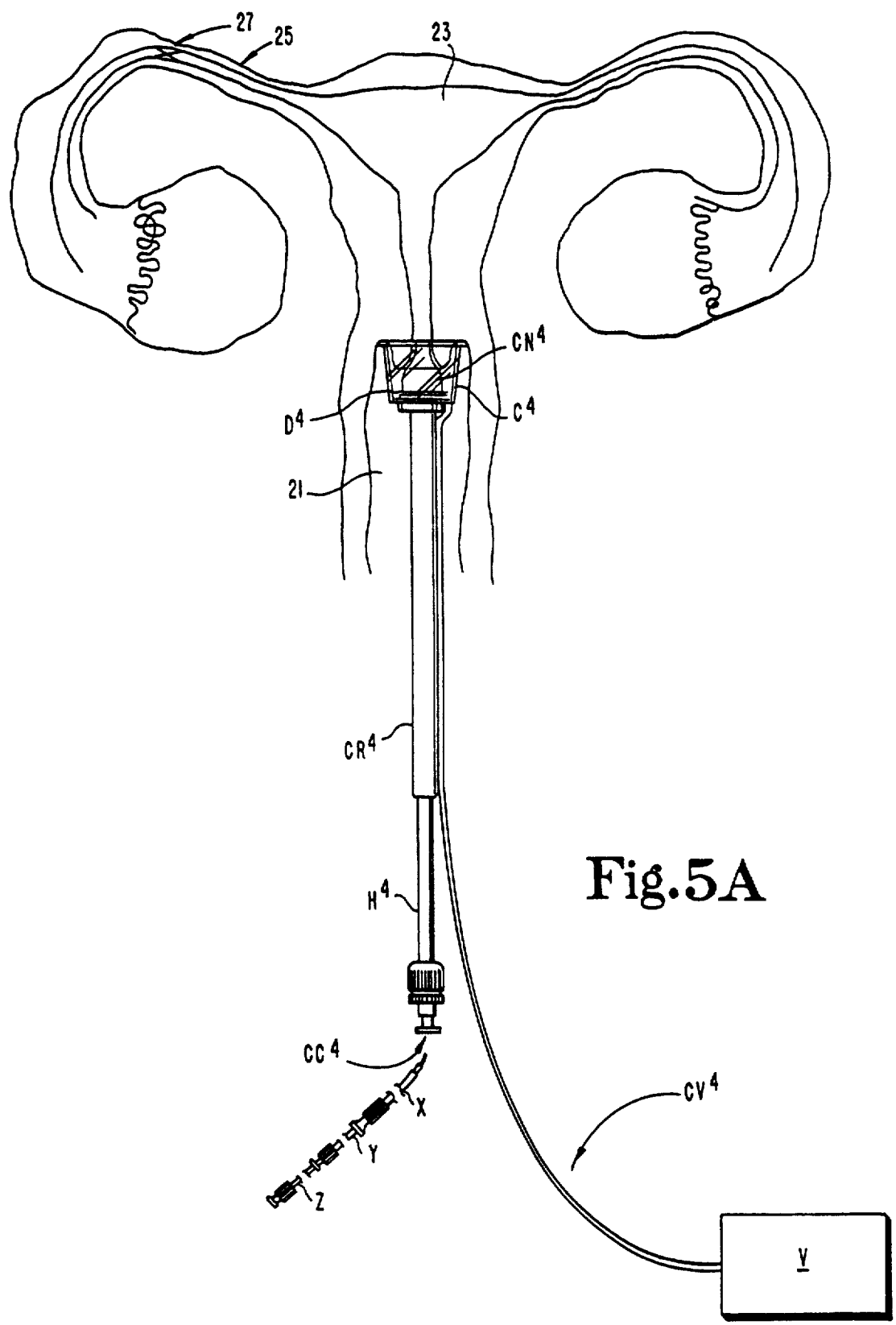
FIG. 5A is an anterior view of the method of this invention.
Figure 5B:
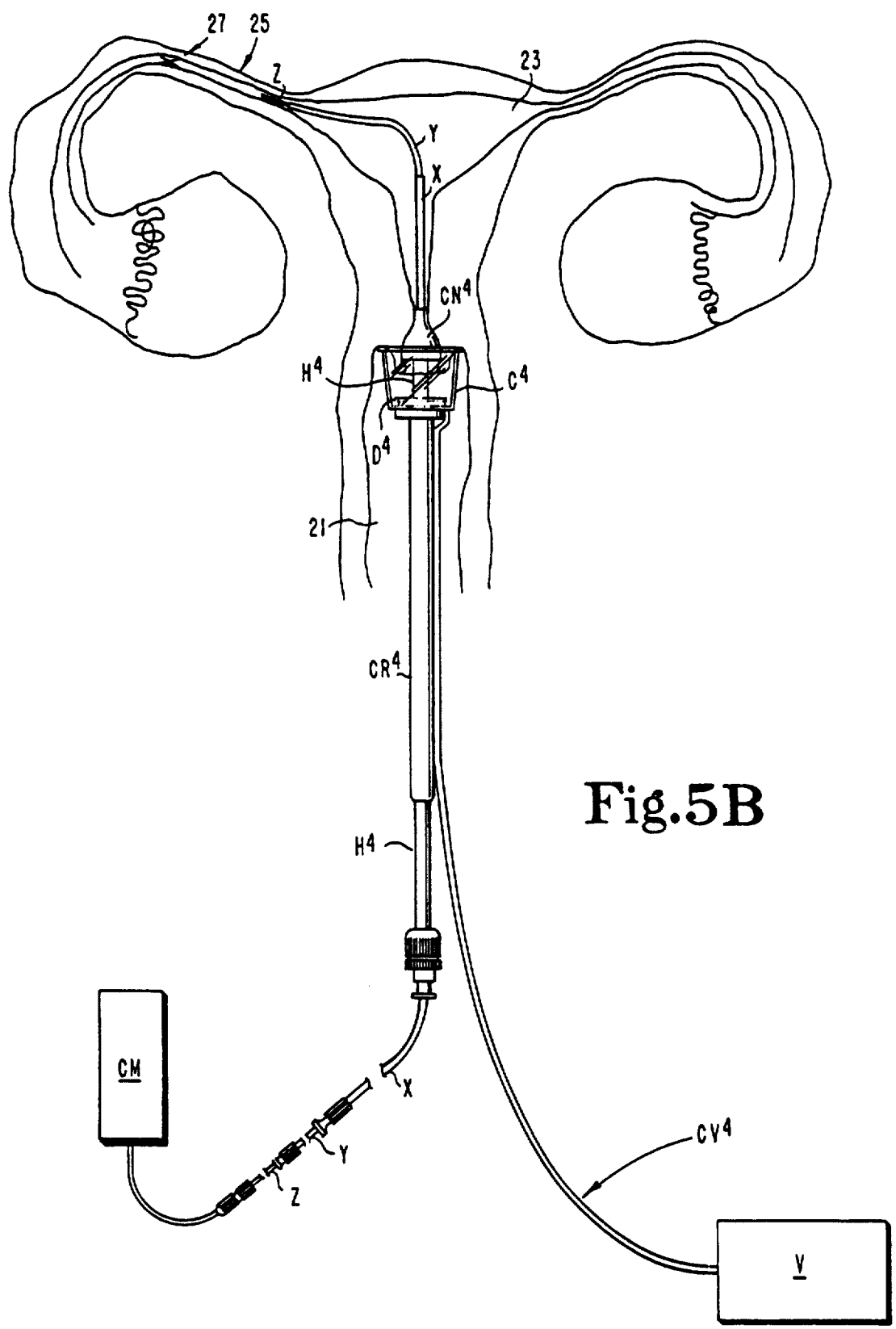
FIG. 5B is a further anterior view of the method of this invention.
Figure 5C:
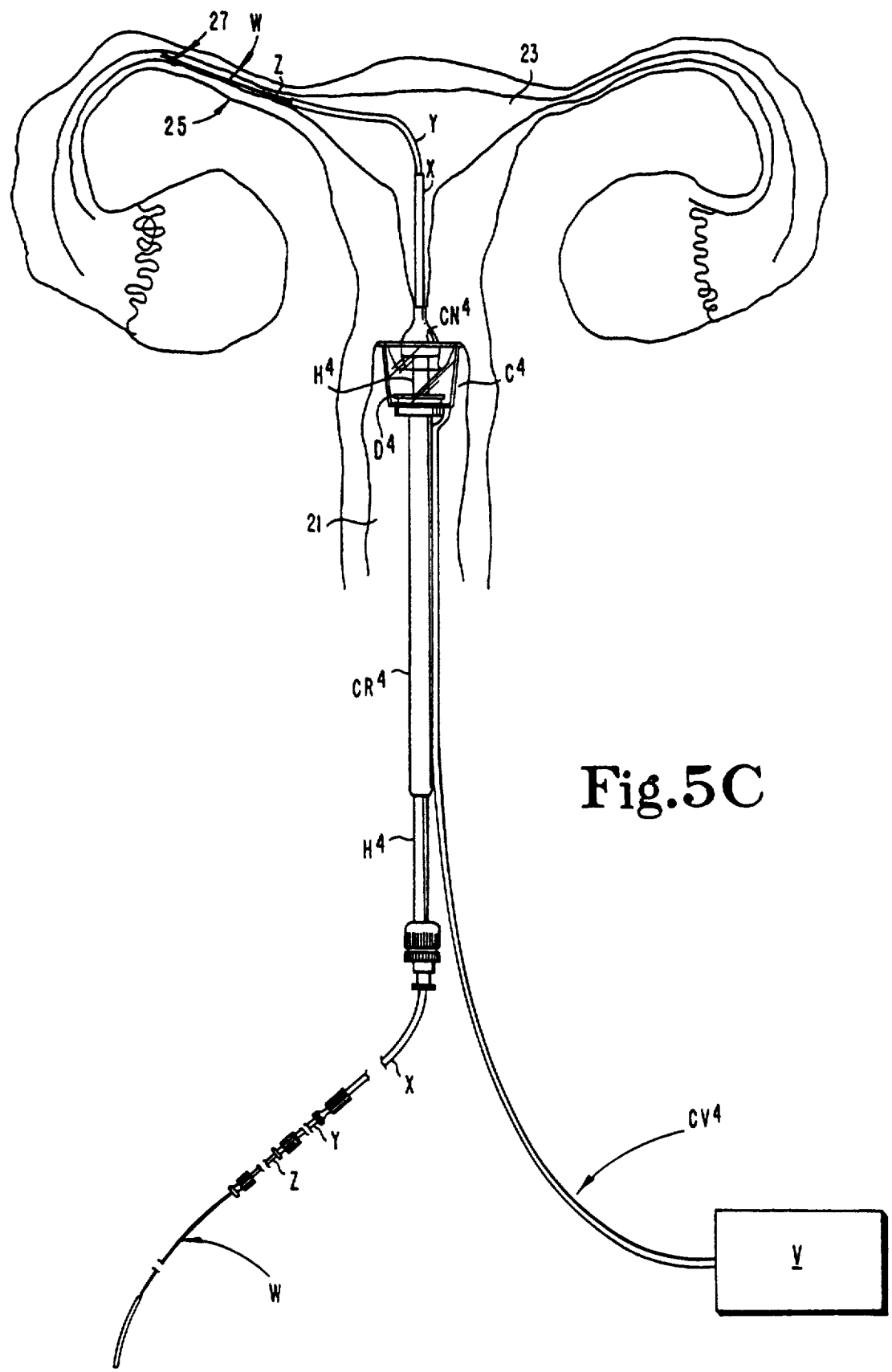
FIG. 5C is a further anterior view of the method of this invention.

FIGS. 5A, 5B, and 5C illustrate a method of this invention being performed on a patient. The patient's vagina 21, uterus 23, and fallopian tube 25 is shown. Fallopian tube 25, as illustrated, is blocked by obstruction 27. The device illustrated is the fourth embodiment of this invention having cup $C^4$, handle $H^4$, collar $CR^4$, perpendicular part $D^4$, and soft, plastic vacuum conduit $CV^4$ as previously described. The cup is preferably a soft or pliable plastic to better adapt to the cervix for sealing. The handle and the surrounding collar when used are preferably flexible plastic to allow bending for greater manipulation and control during use of the present invention.

FIG. 5A illustrates the hysterography device seated on the patient's cervix with handle $H^4$ and collar $CR^4$ positioned transvaginally. Cup $C^4$ is suction seated due to the vacuum applied by vacuum device V connected to conduit $CV^4$ with Luer lock $LL^{4b}$. Vacuum device V may be, for example, a hand vacuum pump such as one offered by Mityvac; Neward Enterprises, Cucamonga, Calif. and disclosed in the July 1988 issue of Radio-Graphics, Volume 8, Number 4, pages 621–640. Cone $CN^4$ is shown recessed in cup $C^4$. The coaxial catheters, catheter X, catheter Y, and catheter Z are shown in position to be inserted into conduit $CC^4$.

FIG. 5B illustrates cone $CN^4$ being moved away from cup $C^4$ and up into the cervical canal of the patient for the purposes of a more complete seal. Movement of the cone $CN^4$ is accomplished by moving handle $H^4$ upward with respect to collar $CR^4$. Note that the collar, in the preferred embodiment, is affixed to the cup with, for example, adhesive; and likewise, the cone is affixed to the handle with, for example, adhesive. FIG. 5B also illustrates catheters X, Y, and Z inserted in the conduit in handle $H^4$, and into the uterus 23. Catheter Z is inserted into fallopian tube 25 at its distal end, and is attached to a source of contrast media CM at its proximal end. Contrast media is injected into the fallopian tube 25 to allow fluoroscopic examination thereof, including diagnosis of obstruction 27. Cup $C^4$ and cone $CN^4$ provide a seal with the cervix to contain the contrast media.

FIG. 5C illustrates catheter Z being detached from contrast media source CM, and having guide wire W inserted in the lumen of catheter Z. The guide wire W is advanced in the lumen, out of the distal end of catheter Z, and into the fallopian tube 25. Guide wire W is advanced against obstruction 27 with a poking action, working through the obstruction to open it. Thus treatment of the obstruction, potentially causing infertility, is accomplished. Thereafter, contrast media may be again injected, as set forth in the description accompanying FIG. 5B, to determine the extent of opening of the obstruction.

As earlier described, the introduction of a fiberoptic device through the lumens of the catheters in conduit $CC^4$ may be done for direct visual inspection in the uterine cavity. The timing and sequence of injection of contrast media, advancing of guide wires, and introduction of fiberoptic devices may vary from case to case depending on the diagnosis and treatment required.

All publications and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be practiced within the scope of the appended claims.

What is claimed is:

1. A hysterography device for penetrating an obstruction in a patient's fallopian tube comprising:
   a handle containing a first conduit, wherein said handle comprises a plastic tube which is flexible;
   a cup located at a first end of said handle, said cup designed to fit the cervix of a patient;
   means for applying a vacuum within said cup; and
   a cone located within said cup having a nose designed to penetrate into the introitus of the cervical canal of said patient;
   means for injecting a liquid contrast media through said cone and into a patient's uterine cavity for radiography thereof;
   a first catheter having a first lumen and located in said first conduit;
   a wire guide for penetrating an obstruction in a patient's fallopian tube; and,
   a second catheter disposed in said first lumen and having a second lumen, a third catheter disposed in said second lumen and having a third lumen, wherein said wire guide is disposed in said third lumen.

2. The device of claim 1 wherein said means for applying a vacuum includes a tube which is independent from said handle, said tube being connected to said cup.

3. The device of claim 2 wherein said cup and said cone are movable with respect to each other providing adaptation to the cervix of the cup and variable penetration of the conduit with the cone into the cervical canal for the purpose of a seal.

4. A hysterography device comprising:
   a handle containing a first conduit;
   a cup located at a first end of said handle, said cup designed to fit the cervix of a patient;
   means for applying a vacuum within said cup;
   a cone located within said cup having a nose designed to penetrate into the introitus of the cervical canal of said patient;
   a first catheter disposed in said first conduit and having a first lumen;
   a second catheter disposed in said first lumen and having a second lumen;
   a third catheter disposed in said second lumen and having a third lumen; and,
   a wire guide disposed in said third lumen for penetrating an obstruction in a patient's fallopian tube.

5. The device of claim 4 wherein said cup and said cone are movable with respect to each other providing adaptation to the cervix of the cup and variable penetration of the conduit with the cone into the cervical canal for the purpose of a seal.

6. The method of providing non-invasive entry into the uterine cavity of a patient and of penetrating an obstruction in the patient's fallopian tube, comprising the steps of:
   suction sealing a cup of a hysterography device to the cervix of the patient, said hysterography device having a handle with a first conduit sized to receive a catheter therein and further having means for injecting a liquid contrast media into a patient's uterine cavity for radiography thereof;
   injecting liquid contrast media through said means for injecting and into the uterine cavity;

introducing a first catheter having a lumen through said first conduit and into the uterine cavity of the patient; and advancing a guide wire through said catheter lumen and in the fallopian tube against an obstruction therein and opening the obstruction in the fallopian tube with said guide wire.

7. The method of claim 6 and further comprising the step of injecting a contrast media through said catheter lumen into the fallopian tube.

8. The method of claim 7 wherein said introducing step includes the step of introducing a second catheter disposed in said first lumen and having a second lumen, and introducing a third catheter disposed in said second lumen.

9. The method of claim 8 and including a cone movable with respect to said cup, said cone having said conduit therein, and further comprising the step of moving said cone away from said cup and into the cervical canal providing a seal.

10. The method of claim 9 wherein said cup is made of soft plastic and wherein, during said suction seating step, said cup is pliable to adapt to the cervix of the patient.

11. The method of claim 10 wherein said handle is made of a flexible plastic material allowing operator manipulation thereof during said advancing step.

12. The method of claim 7 wherein said step of injecting said contrast media occurs before said step of advancing said guide wire against the obstruction.

13. The method of claim 7 wherein said step of injecting said contrast media occurs after said step of advancing said guide wire against the obstruction.

14. The method of claim 6 and including a cone movable with respect to said cup, said cone having said conduit therein, and further comprising the step of moving said cone away from said cup and into the cervical canal providing a seal.

15. The method of claim 6 wherein said cup is made of soft plastic and wherein, during said suction seating step, said cup is pliable to adapt to the cervix of the patient.

16. The method of claim 6 wherein said handle is made of a flexible plastic material allowing operator manipulation thereof during said advancing step.

17. The method of providing non-invasive entry into the uterine cavity of a patient and of penetrating an obstruction in the patient's fallopian tube, comprising the steps of:

suction sealing a cup of a hysterography device to the cervix of the patient, said hysterography device having a handle with a first conduit sized to receive a catheter therein;

introducing a first catheter having a lumen through said first conduit and into the uterine cavity of the patient; and advancing a guide wire through said catheter lumen and in the fallopian tube against an obstruction therein and opening the obstruction in the fallopian tube with said guide wire;

wherein said introducing step includes the step of introducing a second catheter disposed in said first lumen and having a second lumen, and introducing a third catheter disposed in said second lumen.

* * * * *

UNITED STATES PATENT AND TRADEMARK OFFICE
CERTIFICATE OF CORRECTION

PATENT NO. : 5,259,836
DATED : November 9, 1993
INVENTOR(S) : Amy S. Thurmond et al.

It is certified that error appears in the above-indentified patent and that said Letters Patent is hereby corrected as shown below:

Col. 3, line 43, please change "outaway" to --cutaway--.

Col. 4, line 12, please change "aids" to --axis--.

Col. 4, line 54, please insert --hysterograph-- after "the".

Signed and Sealed this

Fourteenth Day of March, 1995

Attest:

BRUCE LEHMAN

*Attesting Officer*          *Commissioner of Patents and Trademarks*